Feb. 22, 1966 N. E. CANINE Plant Pat. 2,603
GLADIOLUS PLANT
Filed Oct. 14, 1964
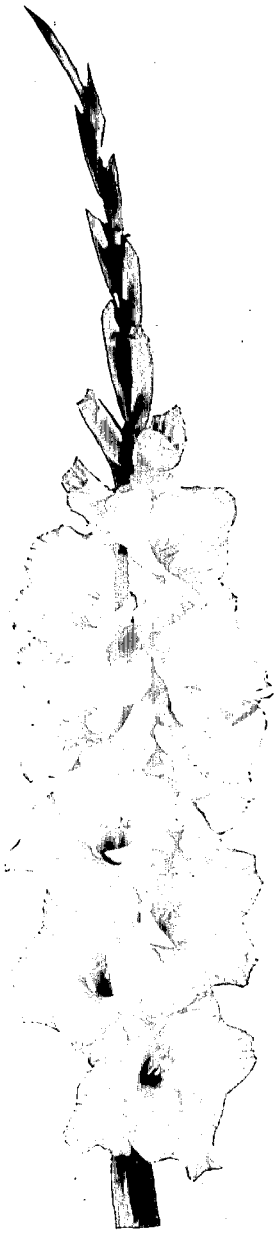
INVENTOR
Neil E. Canine
By Lamont Johnston
ATTORNEY United States Patent Office Plant Pat. 2,603
Patented Feb. 22, 1966

2,603
GLADIOLUS PLANT

Neil E. Canine, Hayward, Calif., assignor to Selected Glads, Inc., New Albany, Ind., a corporation of Tennessee Filed Oct. 14, 1964, Ser. No. 403,963
1 Claim. (Plt.—85)

My present invention relates to a new and improved variety of gladiolus and is notable for its deeper, improved Traveler color (light rose-pink), for its general vigor, ability to show many buds in color before opening and its ability to open well from tight bud.

This new variety is a mutation or "sport" of the variety, Traveler (unpatented).

This new variety has been asexually reproduced by me in California by natural increase from cormels through several generations and its characteristics have proven to be permanently fixed.

The illustration, made a part of this application, shows a single bloom spike, reduced in size, and is as nearly true to color as it is possible to depict. The illustration shows quite accurately the color, placement, the large size of the floret and the spike formation.

In the following detailed description, color plate references are to "The Horticultural Colour Chart" by the British Colour Council. Where there are other references to color, the ordinary dictionary meanings of the terms are intended.

*The plant*

Growth: Strong grower; attains a height of 55 inches, over-all.

Blooming: Blooms in 90 days from large bulbs.

Stems: Straight stem is ⅜–½ inch in diameter. Color is rose above the bulb.

Foliage: Plant is broad, upright and fan-shaped. Leaves average 1¾ inches across. Plant foliage, excluding the flower spike, is 34 inches high.

Disease resistance: This variety has been found to be unusually healthy and free of disease.

Corms: Large, well-husked. Husk is deep rose; flesh is unusual terra cotta color with a slight deep rose shading near husk line.

*The flower*

Spike: Flowerhead is 24 inches in length, with seventeen to eighteen buds of which seven to eight are open at once.

Bud:

*Size.*—Opening buds are 2½ to 3 inches long.

*Opening.*—Six to eight show color.

Flower:

*Arrangement.*—Florets are semi-formally placed.

*Size.*—Individual florets are 5 inches in diameter.

*Form.*—Double triangle, one inside the other giving a six-pointed effect. Florets are ruffled.

*Keeping qualities.*—Opens well on the plant; also from a tight bud when cut.

Petals:

*Shape.*—Triangular; ruffled.

*Size.*—Upper petals, 2 inches across; lip petals, 1⅛ inches.

*Aspect.*—Average substance.

*Fragrance.*—None.

*Color.*—Inner triangle of petals is Rhodamine Pink $527/_3$ at lightest to $527/_1$ at edges. Feather blotch on lips is deepest shade of Rhodamine Pink, 527. Outer triangle is Dawn Pink $523/_2$ with flecks of 523. Reverse of outer triangle is Dawn Pink $523/_1$ and flecks 523. Reverse of inner triangle is streaked with Rhodamine Pink 527. Calyx is deep pink.

Reproductive organs:

*Stamens.*—Purple.

*Pistil.*—Rose Pink 427.

*Comparisons*

My new variety resembles Traveler (unpatented), of which it is a mutation or "sport," but differs principally as follows:

(1) The color is deeper and more intense.

(2) It has more vigor.

(3) The color does not fade as much when opened from a tight bud.

Having thus disclosed my invention, I claim:

The new and distinct variety of gladiolus plant, substantially as herein shown and described, characterized by its unique blossom color, vigor, ruffling, straight flowering spikes, excellent opening qualities, and retention of color when opened from a tight bud.

No references cited.

ABRAHAM G. STONE, *Primary Examiner.*

R. E. BAGWILL, *Assistant Examiner.*